United States Patent
Cane' et al.

(10) Patent No.: US 12,246,161 B2
(45) Date of Patent: Mar. 11, 2025

(54) SHELL FOR A PORTABLE ELECTROMECHANICAL APPARATUS FOR DRUG INFUSION

(71) Applicant: CANE' S.P.A., Rivoli (IT)

(72) Inventors: Claudio Cane', Rivoli (IT); Mario Cane', Rivoli (IT); Paolo Cane', Rivoli (IT)

(73) Assignee: CANE' S.P.A., Rivoli (IT)

( * ) Notice: Subject to any disclaimer, the term of this patent is extended or adjusted under 35 U.S.C. 154(b) by 827 days.

(21) Appl. No.: 17/417,820

(22) PCT Filed: Dec. 24, 2019

(86) PCT No.: PCT/IB2019/061336
§ 371 (c)(1),
(2) Date: Jun. 24, 2021

(87) PCT Pub. No.: WO2020/141412
PCT Pub. Date: Jul. 9, 2020

(65) Prior Publication Data
US 2022/0072221 A1 Mar. 10, 2022

(30) Foreign Application Priority Data
Dec. 31, 2018 (IT) .......................... 102018000021493

(51) Int. Cl.
*A61M 5/142* (2006.01)
*A61M 5/145* (2006.01)

(52) U.S. Cl.
CPC .... *A61M 5/14236* (2013.01); *A61M 5/14546* (2013.01)

(58) Field of Classification Search
CPC .... A61M 2005/14573; A61M 5/14546; A61M 2005/14553; A61M 5/14236; A61M 5/14244; A61M 5/14566
See application file for complete search history.

(56) References Cited

U.S. PATENT DOCUMENTS

| 4,273,122 A * | 6/1981 | Whitney ............... A61M 39/04 604/67 |
| 4,664,299 A * | 5/1987 | Goncalves ......... B65D 83/0005 222/386 |
| 5,269,762 A * | 12/1993 | Armbruster ............. A61M 5/20 604/131 |
| 6,447,487 B1 | 9/2002 | Cane' |

(Continued)

FOREIGN PATENT DOCUMENTS

| EP | 2174679 A1 | 4/2010 |
| EP | 2394682 B1 * | 3/2016 ........ A61M 5/14566 |

OTHER PUBLICATIONS

International Search Report and Written Opinion of the International Searching Authority issued for International PCT Application No. PCT/IB2019/061336 on Apr. 28, 2020.

*Primary Examiner* — Quynh-Nhu H. Vu
(74) *Attorney, Agent, or Firm* — Howson & Howson LLP (57) ABSTRACT

Shell (11) for a portable electromechanical apparatus for drug infusion, comprising an outer casing (13) and a support structure (15) housed within the casing (13), wherein said casing (13) has a monolithic ring shape and is entirely made of plastics, and wherein said support structure (15) is at least partially made of metal.

10 Claims, 6 Drawing Sheets

(56) References Cited

U.S. PATENT DOCUMENTS

| | | | |
|---|---|---|---|
| 6,854,620 B2 * | 2/2005 | Ramey | A61M 5/1456 |
| | | | 222/327 |
| D565,176 S | 3/2008 | Cane' | |
| D659,234 S | 5/2012 | Cane' | |
| 8,172,814 B2 | 5/2012 | Cane' | |
| 8,343,099 B2 * | 1/2013 | Peter | A61M 5/14566 |
| | | | 604/154 |
| 9,220,835 B2 | 12/2015 | Cane' | |
| 9,289,549 B2 | 3/2016 | Cane' | |
| 9,463,271 B2 | 10/2016 | Cane' | |
| 10,406,283 B2 | 9/2019 | Cane' et al. | |
| 2006/0184124 A1 * | 8/2006 | Cowan | A61M 5/16827 |
| | | | 604/155 |
| 2010/0192094 A1 | 7/2010 | Jeha et al. | |
| 2014/0052055 A1 | 2/2014 | Yodfat et al. | |
| 2014/0361048 A1 * | 12/2014 | Cane' | A61M 5/1456 |
| | | | 222/386 |
| 2017/0340810 A1 * | 11/2017 | Cane' | A61M 5/14546 |
| 2018/0008787 A1 * | 1/2018 | Schriver | A61M 5/365 |
| 2018/0185584 A1 | 7/2018 | Cowe et al. | |
| 2019/0209772 A1 * | 7/2019 | Cane' | A61M 5/16827 |
| 2020/0016328 A1 | 1/2020 | Cane' et al. | |
| 2020/0046899 A1 | 2/2020 | Cane' et al. | |

\* cited by examiner

SHELL FOR A PORTABLE ELECTROMECHANICAL APPARATUS FOR DRUG INFUSION

TECHNICAL FIELD

The present invention relates to a shell for a portable electromechanical apparatus for drug infusion. The invention falls within the field of electromedical apparatus, intended for the infusion of drugs in liquid form into the body of a living being. More particularly, the invention relates to a shell for an electromechanical apparatus of the portable type, i.e. which can be "worn" by a patient, for example by means of a suitable case or pouch or the like, for infusing drugs through a syringe removably engaged in the shell.

BACKGROUND ART

Electromechanical apparatus for infusing drugs in liquid form are known in the field of electromedical apparatus. The infusion of the drug takes place through a syringe that is mechanically connected to the apparatus and hydraulically connected to a living being. The hydraulic connection is usually effected through a cannula and a needle implanted in the body of a living being.

An example of a known electromechanical apparatus for drug infusion is described in EP 2 174 679 A1. The operation of this type of apparatus is based on mechanical parts that transform the rotational motion of an electric geared motor into the translational motion of a pusher intended to exert an adequate thrust against the plunger of the syringe connected to the apparatus. The transformation of the motion from rotational to translational is carried out by means of an electromechanical drive unit.

In the apparatus of known type, the drive unit is housed in a casing and the various parts of the unit are fixed to the casing by screws or mortise couplings or the like.

A drawback of this kind of arrangements derives from the assembling complexity, which also causes high manufacturing and maintenance costs.

A main object of the invention is therefore to solve the prior art drawbacks by providing a shell for a portable electromechanical apparatus for drug infusion, that allows easy installation and maintenance of the electromechanical parts.

Another drawback of known portable infusion apparatus is their excessive weight. As is well known, the main components of the apparatus that determine its weight are the geared motor, the mechanical parts for the transmission of motion, the casing and the battery that powers the electric geared motor. Since these infusion apparatus are especially intended to be worn by an individual, it is clear that the lighter they are, the more they will be appreciated by users.

A further object of the present invention is therefore to provide a shell that has reduced weight and can therefore be used for the making of easily portable apparatus.

Last but not least, a drawback of known apparatus, which arises from the assembling complexity and the presence of several components coupled to one another, is caused by the noise that is generated by the mechanical transmission and propagates outside the shell during operation of the apparatus. As apparatus for drug infusion are often worn by individuals in the course of normal activity, noise can be a particularly annoying and undesirable factor and can impair the spread of this type of electromedical apparatus among patients.

A further object of the invention is therefore to provide a shell of the aforementioned type which allows to make electromedical apparatus for drug infusion through a disposable syringe and is more silent in operation than the known electromechanical infusion apparatus.

A further object of the invention is to provide a shell for infusion apparatus that that lends itself to being made in a compact and portable format, i.e. that can be easily worn by the user, even in those situations where noise during operation could be annoying.

A still further object of the invention is to provide a shell for a portable apparatus for drug infusion which has a high hydraulic sealing capacity and can therefore be worn by users even in damp environments, such as during normal body care and washing activities.

A last but not least object of the invention is to provide a device for drug infusion, which is simple and inexpensive to implement and is therefore suitable for large-scale industrial production.

These and other objects are achieved with a shell for a portable electromechanical apparatus for drug infusion as claimed in the appended claims.

SUMMARY OF THE INVENTION

According to the invention, the shell for a portable electromechanical apparatus for drug infusion mainly comprises an outer casing and a support structure housed, preferably in a removable manner, within the casing. Advantageously, according to the invention, the casing has a monolithic ring shape and is entirely made of plastics; preferably, the ring-shaped structure of the monolithic casing is substantially rectangular or square in plan, possibly with one or more rounded flanks that are convex towards the outside of the casing, and the flanks of the casing have substantially the same width over the entire perimeter, so as to obtain high stiffness and strength of the structure. In addition, still according to the invention, said support structure is at least partially made of metal. Even more preferably, according to the invention, the support structure is entirely made of metal, preferably aluminum.

According to a preferred embodiment of the invention, said casing defines a shape substantially rectangular in plan and defines therein a chamber with corresponding parallelepiped shape, in which said support structure is housed. In other embodiments, the casing may define annular shapes of any kind, for example circular or oval shapes, or shapes with square or hexagonal plan.

Preferably, according to the invention, the casing surrounds at least four flanks of said chamber and at least one of its opposite bases is open. According to a preferred embodiment of the invention, said at least one open base is one of the major bases of the casing of the shell. In addition, still according to a preferred embodiment of the invention, said at least one open base can be closed by a lid that can be removed in order to get access to the chamber enclosed within the casing.

Preferably, the casing further comprises a coupling ferrule for firmly connecting a syringe to the shell of the apparatus. The ferrule preferably defines a bayonet-like coupling for said syringe. In addition, the ferrule is preferably incorporated in the body of said casing, i.e. it is obtained as a single piece with the body of the casing with the same molding process.

Preferably, therefore, said ferrule defines a bayonet-like coupling for a syringe provided with wings extending radially towards the outside at the base of the syringe and comprises a pair of opposite arched seats and a pair of diametrically opposite slits, whereby the syringe can be engaged into the shell by a coupling movement substantially comprising an axial approaching movement and a subsequent rotation about the axis of the syringe. In other embodiments, the ferrule may define other types of coupling for the base of a syringe of a different kind, for example a syringe having a screw or complementary coupling provided inside or outside the syringe body.

The shell according to the invention preferably comprises a guide member incorporated in the body of said casing. Said guide member is advantageously capable of guiding the longitudinal sliding of a longitudinally slidable rod and of exerting an axial thrust onto the plunger of a syringe associated with the shell of the apparatus through the aforementioned ferrule.

Advantageously, according to the invention, the support structure is preferably entirely made of metal, for example aluminum, in order to confer stiffness and strength, and it comprises a base plate and a frame fixed to the plate, for example by means of screws. Advantageously, between the base plate and the frame there is defined a seat capable of housing the mechanical parts of an electromechanical drive unit, arranged to cause delivery of a drug from a syringe removably engaged in the shell. In addition, the base plate is preferably substantially flat and, when housed in the chamber defined within the casing of the shell, rests against a plurality of rest elements incorporated in the casing and extending longitudinally and transversely within the chamber of the casing of the shell. The support structure is firmly but detachably associated within the casing of the shell, preferably in a position distal to said guide member.

An electric geared motor and the contacts for a battery powering said electric geared motor can also be fixed to the frame. The battery may also be accessible through a door provided on the adjacent flank of the casing of the shell.

Advantageously, according to a particular embodiment of the invention, the longitudinally slidable rod and the guide member both have a non-circular cross-section, whereby rotation of the rod relative to the guide member is prevented. Preferably, the cross-section of the rod and of the guide member is oval or elliptical, but other geometrical shapes are possible, preferably comprising at least one curved portion and at least one rectilinear portion, such as, for example, "C"-like or "D"-like shapes.

Preferably, according to the invention, the cross-section of the rod and the cross-section of the guide member are complementary to each other. Even more preferably, a minimum clearance is defined between the rod and the guide member, such as to allow axial sliding of the rod without jamming, but also to prevent oscillations of the rod relative to the guide member.

More generally, the shell according to the invention is advantageously capable of housing an electromechanical unit for causing delivery of a drug through a syringe removably engaged in the shell. The electromechanical unit may be of the kind having a rod longitudinally slidable within a guide member and capable of exerting an axial thrust onto the plunger of the syringe engaged in the infusion apparatus. In order to prevent the rod from rotating relative to the guide member during longitudinal sliding, the rod and the guide member preferably have a non-circular cross-section.

The rod preferably comprises an axial cavity having at least one open base and adapted to receive a rotatable screw actuated by an electric geared motor belonging to said electromechanical unit. The rotatable screw is engaged with the corresponding thread of an internally threaded nut or bushing housed within said cavity, preferably at said open base. Preferably, said nut or bushing is co-molded with or press-fitted in the open base of the longitudinally slidable hollow rod. The electromechanical unit may further comprise an electric geared motor having a driving shaft provided with a pinion, which, with its teeth, engages into a toothed gear wheel fixed to the base of said screw. The electric geared motor is adapted to cause, through coupling between the pinion and the toothed gear wheel, rotation of the screw in both directions, depending on the direction of rotation of the electric geared motor, and consequent sliding back and forth of the hollow rod.

According to the invention, the casing of the shell is made of a plastic material, preferably by means of the injection molding technique, and said guide member, if provided, is molded during forming of said casing and thus forms a single piece with said casing.

The guide member extends longitudinally preferably outside the casing of the shell. In other embodiments, however, it can also be envisaged that the guide member extends inside the casing or both inside and outside said casing.

Preferably, in addition, the guide member comprises an annular gasket housed within an axial cavity and adapted to exert a hydraulic tight-fit action against the outer surface of the rod, thus contributing to make the apparatus substantially waterproof. The gasket is preferably housed in an annular groove open radially towards the inside of the cavity of the guide member and longitudinally outside the guide member and therefore has a substantially "L"-shaped cross-section. The gasket is also preferably held in position by a locking cap, which is axially fitted on the guide member and prevents the gasket from slipping out of said groove.

The guide member may be surrounded by said engaging ferrule for the open base of a syringe for drug infusion, whereby, when the syringe is engaged in the ferrule and the guide member extends outside the casing, the guide member extends over a portion of the length of the hollow body of the syringe.

The longitudinally slidable hollow rod may comprise an integrated distal portion or pusher, said pusher being provided with an annular portion extending radially towards the outside of the rod, and a longitudinal portion extending axially from said annular portion. Said pusher is apt to be received in a seat provided in the sliding plunger which causes delivery of the drug from a syringe.

In other embodiments, a pusher separated from the slidable rod and fixed to the rod by known means, for example glue or mortise, may be provided.

Preferably, said seat provided in the plunger receives the pusher with some interference, in order to prevent occurrence of the so-called free-flow phenomenon, i.e. the exit of the drug from the syringe also in the absence of infusion by the apparatus, because of the difference in hydrostatic pressure due to the position in which the apparatus may be arranged relative to the patient's body associated with the apparatus.

Advantageously, according to a preferred embodiment of the invention, the casing, the engaging ferrule for the syringe, the guide member, the slidable rod and the pusher are entirely made of plastics, for example of the same plastic material and by means of the injection molding technique. Thanks to the wide use of plastics in the making of pump components, a remarkable reduction in weight is thus obtained and this contributes to make transport of the pump by the user easier.

In a particular embodiment of the invention, the shell is provided with a protective bell for the syringe associated with the infusion apparatus. The bell mainly comprises a pair of half-shells preferably hinged at the base. The half-shells are preferably hinged to the coupling ferrule for the syringe, which ferrule is in turn preferably incorporated in the body of the casing. Advantageously, according to this particular embodiment of the invention, the half-shells can assume, by rotating continuously about the hinge pins, an open configuration, in which the syringe is accessible to be inserted into and removed from the shell, and a closed configuration, in which the syringe is substantially completely hidden from view. The half-shells also preferably have a substantially "C"-shaped cross-section and consequently define inside them, when closed, a corresponding substantially cylindrical chamber to house the syringe. Advantageously, the half-shells preferably have on the top, i.e. on the side opposite to the hinge pins, a transverse base with a corresponding recess defining a corresponding passage, when the half-shells are closed, for the front end of the syringe from which the drug comes out during infusion. Advantageously, in addition, the half-shells, when closed, define a substantially oval cross-section for said bell and are made in such a way as to be aesthetically integrated in the body of the shell, following the external profile thereof. Said half-shells are also preferably made of plastics, of the same material as the casing.

BRIEF DESCRIPTION OF THE DRAWINGS

Some preferred embodiments of the invention will be described below by way of non-limiting example with reference to the annexed drawings, in which.

In all the figures, the same reference numerals have been used to indicate same or functionally equivalent elements.

DESCRIPTION OF SOME PREFERRED EMBODIMENTS

Referring to the annexed figures, the shell for a portable electromechanical apparatus for drug infusion has been indicated as a whole with reference numeral 11.

According to the invention, the shell 11 mainly comprises an outer casing 13 and a support structure 15 housed within the casing 13. Advantageously, according to the invention, the casing 13 has a monolithic ring shape and is entirely made of plastics, preferably by means of the injection molding technique. In addition, still according to the invention, said support structure 15 is at least partially made of metal, preferably aluminum.

According to the invention, the ring-shaped structure of the monolithic casing 13 is substantially rectangular or square in plan, possibly with one or more rounded flanks that are convex towards the outside of the casing, and the flanks of the casing 13 have substantially the same width "d" over the entire perimeter, so as to obtain high stiffness and strength of the structure.

According to the shown embodiment of the invention, said casing 13 defines a shape substantially rectangular in plan with a convex flank 13a and defines therein a chamber 17 of corresponding shape in which said support structure 15 is housed. In other embodiments, the casing 13 may define annular shapes of any kind, for example circular or oval shapes, or shapes with square or hexagonal plan. In addition, the width "d" of said casing 13 is constant over the entire perimeter. Preferably, the convex flank 13a corresponds to the flank of the casing 13 on which the stresses generated during drug infusion are discharged.

As can be appreciated in the annexed figures, the casing 13 surrounds at least four flanks of said chamber 17 and comprises both opposite, open major bases 19, 21. Said open bases 19, 21 can, however, be closed by a corresponding lid that can advantageously be removed in order to get access to the chamber 17 enclosed in the casing 13.

Figure 1:
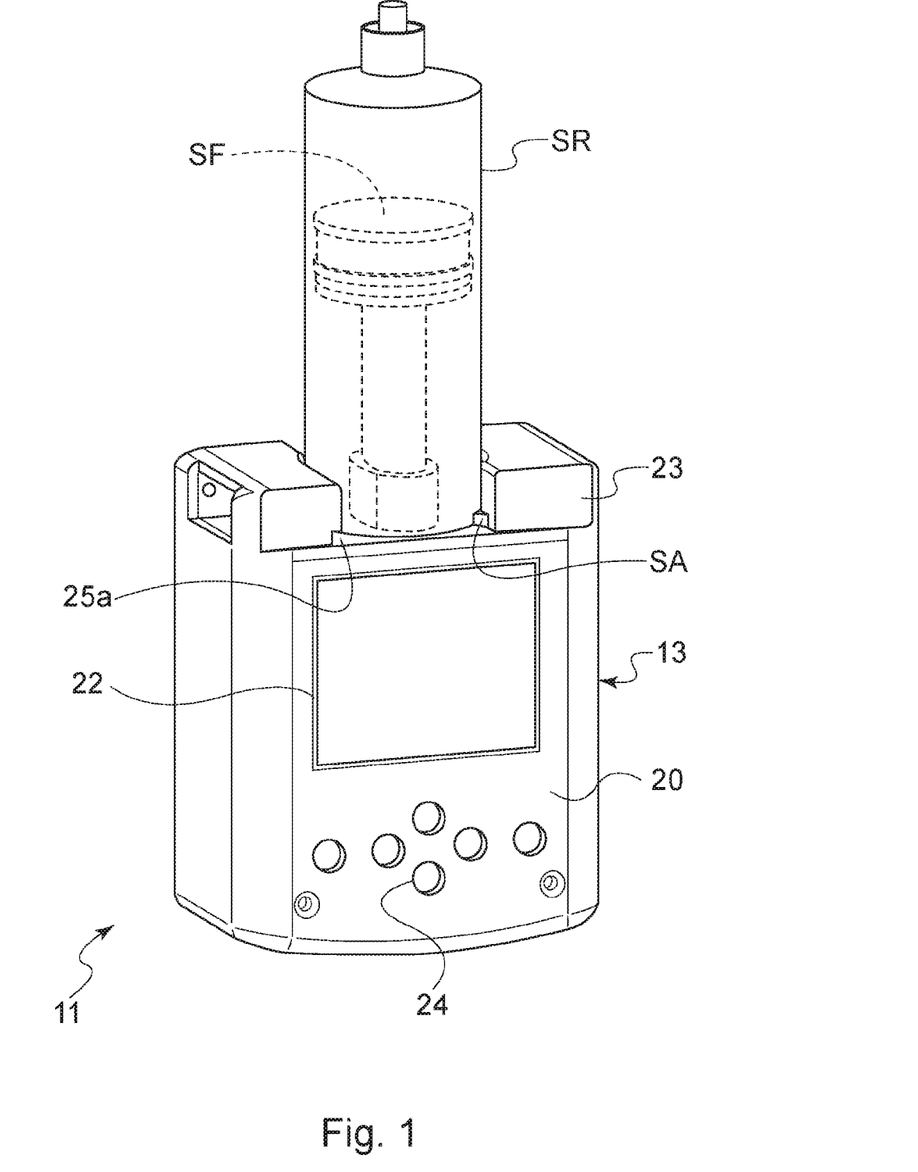
FIG. 1 is a perspective view of a portable electromechanical apparatus for drug infusion that incorporates a shell according to a preferred embodiment of the invention.
Figure 2:
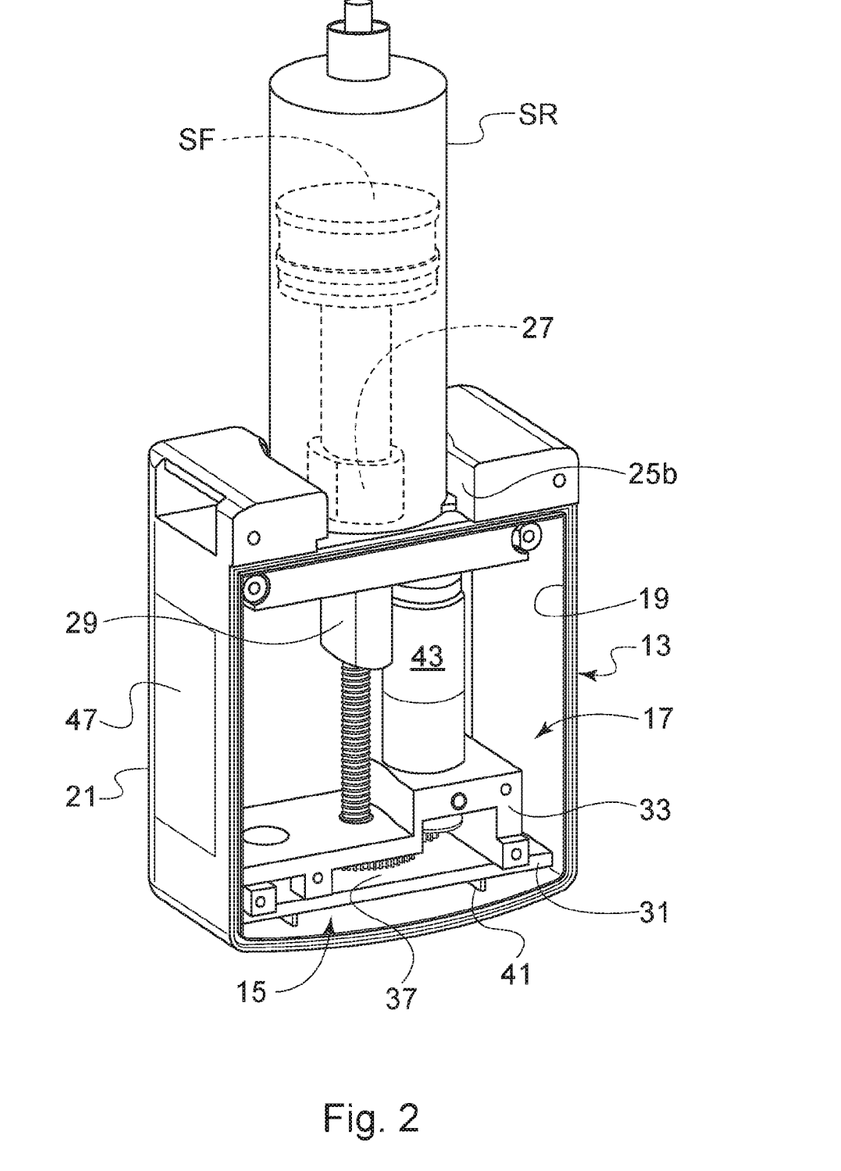
FIG. 2 is a view similar to FIG. 1, in which the front panel of the apparatus has been removed.

Advantageously, the lid closing the open base 19 comprises a front panel 20 in which a display 22 and a set of control and programming keys 24 for controlling the apparatus are incorporated.

The casing 13 comprises, in the illustrated embodiment, a coupling ferrule 23 for firmly connecting a syringe SR to the shell 11 of the apparatus. The ferrule 23 defines a corresponding bayonet-like coupling for said syringe SR. In addition, the ferrule 23 is incorporated in the body of said casing 13, i.e. it is obtained as a single piece with the body of the casing 13 during the molding process for plastic materials.

Said ferrule 23 defines a bayonet-like coupling for a syringe SR provided with wings SA and comprises a pair of opposite arched seats 25a and a pair of diametrically opposite slits 25b, whereby the syringe SR can be engaged into the shell 11 by a coupling movement substantially comprising an axial approaching movement and a subsequent rotation about the axis of the syringe SR. In other embodiments, the ferrule 23 may define other types of coupling for the base of a syringe SR, for example of a syringe having a screw or complementary coupling provided inside or outside the body of the syringe SR.

The shell 11 according to the illustrated embodiment of the invention comprises a guide member 27 incorporated in the body of said casing 13. Said guide member 27 is advantageously capable of guiding the longitudinal sliding of a longitudinally slidable rod 29 and of exerting an axial thrust onto the plunger SF of a syringe SR associated with the shell 11 of the apparatus through the aforementioned ferrule 23.

Advantageously, according to the invention, the support structure 15 is preferably entirely made of metal, for example aluminum, in order to confer stiffness and strength, and it comprises a base plate 31 and a frame 33 fixed to the plate 31 by means of screws. Between the base plate 31 and the frame 33 there is defined a seat 37 capable of housing the mechanical parts of an electromechanical drive unit, arranged to cause exit of a drug from a syringe SR removably engaged in the shell 11. In addition, the base plate 31 is preferably substantially flat and, when housed in the chamber 17 defined within the casing 13 of the shell 11, rests against a plurality of rest elements 41 incorporated in the casing 13 and extending longitudinally and transversely within the chamber 17 of the casing 13 of the shell 11. The support structure 15 is firmly but detachably associated within the casing 13 of the shell 11, preferably in a position distal to said guide member 27.

An electric geared motor 43 and the contacts for a battery (not shown) powering said electric geared motor 43 can also be fixed to the frame 33. The battery may also be accessible through a door 47 provided on the adjacent flank of the casing 13 of the shell 11.

Advantageously, according to a preferred embodiment of the invention, the support structure 15 is housed in the chamber 17 defined by the casing 13, so that the stress exerted by the screw 53 during infusion is discharged against said rest elements 41. Advantageously, the ring-shaped structure of the monolithic casing 13 made of molded plastics and surrounding the chamber 17 brings about the necessary stiffness and strength for bearing the thrust exerted against said rest elements 41.

The longitudinally slidable rod 29 and the guide member 27 both have a non-circular cross-section, whereby rotation of the rod relative to the guide member is prevented.

In the illustrated embodiment, the cross-section of the rod and the cross-section of the guide member are complementary to each other and a minimum clearance is defined between the slidable rod 29 and the guide member 27, such as to allow axial sliding of the rod 29 without jamming, but also to prevent oscillations of the rod 29 relative to the guide member 27.

Still referring to the illustrated embodiment, the cross-section of the rod 29 and of the guide member 27 is oval or elliptical.

Figure 3:
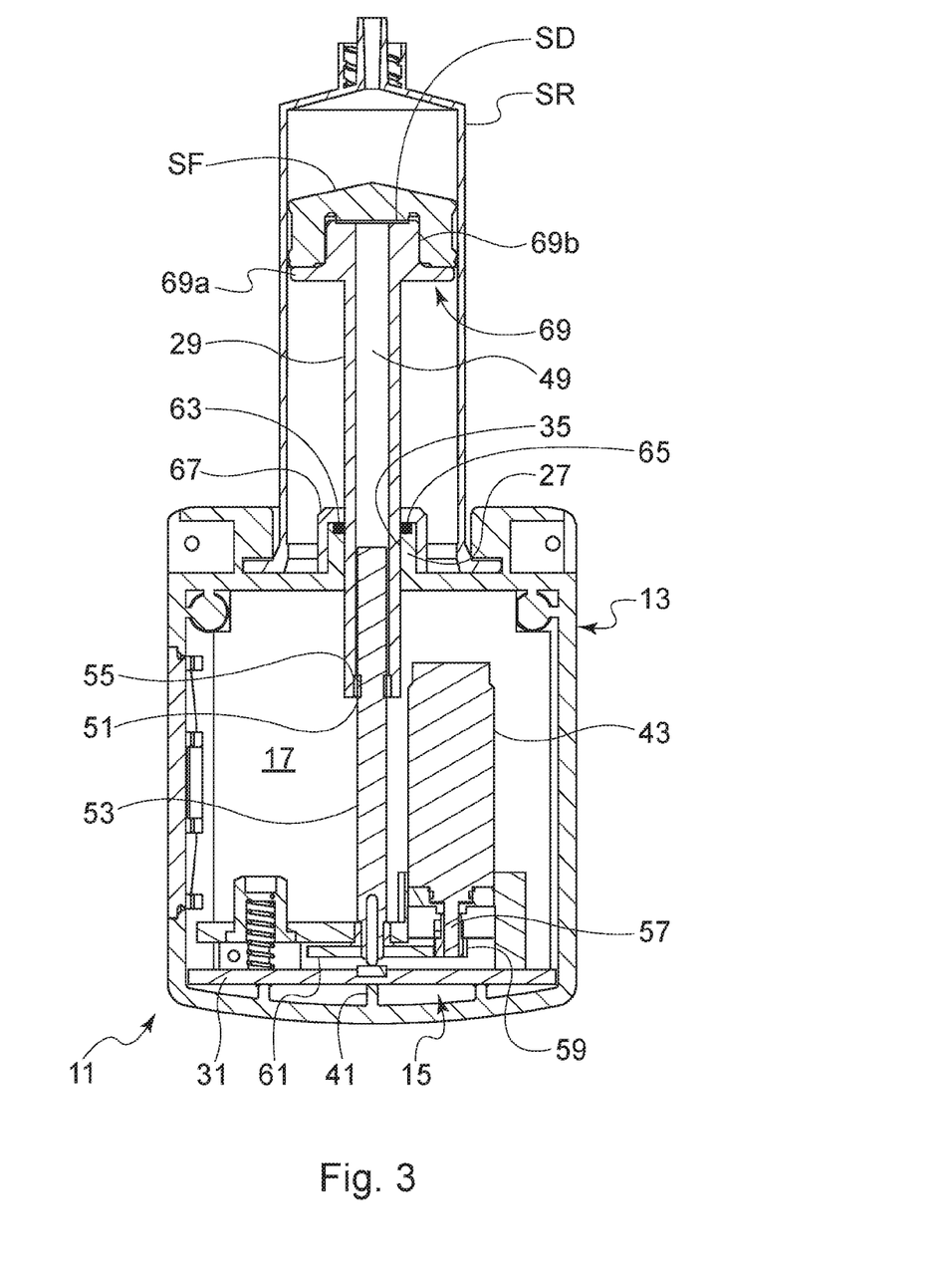
FIG. 3 is a section taken along a longitudinal plane of the apparatus of FIG. 1.

Still referring to the shown embodiment, the rod 29 comprises an axial cavity 49 having at least one open base 51 and is adapted to receive a rotatable screw 53 actuated by an electric geared motor 43 belonging to said electromechanical unit. The rotatable screw 53 is engaged with the corresponding thread of an internally threaded nut or bushing 55 housed within said cavity 49, preferably at said open base 51. Said nut or bushing is co-molded with or press-fitted in the open base 51 of the longitudinally slidable hollow rod 29. The electric geared motor 43 has a driving shaft 57 provided, in turn, with a pinion 59, which, with its teeth, engages into a toothed gear wheel 61 fixed to the base of said screw 53. The electric geared motor 43 is adapted to cause, through coupling between the pinion 59 and the toothed gear wheel 61, rotation of the screw 53 in both directions, depending on the direction of rotation of the electric geared motor, and consequent sliding back and forth of the hollow rod 29.

According to the invention, the casing 13 of the shell 11 is made of a plastic material, preferably by means of the injection molding technique, and said guide member 27, if provided, is molded during forming of said casing 13 and thus forms a single piece with said casing 13.

The guide member 27 extends longitudinally preferably outside the casing 13 of the shell 11. In other embodiments, however, it can also be envisaged that the guide member 27 extends inside the casing 13 or both inside and outside said casing.

Preferably, in addition, the guide member 27 comprises an annular gasket 63 adapted to exert a hydraulic tight-fit action against the outer surface of the rod 29, thus contributing to make the shell 11 substantially waterproof. The gasket 63 is housed, according to the shown embodiment, in an annular groove 65 open radially towards the inside of the cavity 35 of the guide member 27 and longitudinally outside the guide member 27 and is held in position by a locking cap 67, which is axially fitted on the guide member 27 and prevents the gasket 63 from slipping out of said groove 65.

The guide member 27 is surrounded by said engaging ferrule 23 for the open base of a syringe SR for drug infusion, whereby, when the syringe SR is engaged in the ferrule 23 and the guide member 27 extends outside the casing 13, the guide member 27 extends over a portion of the length of the hollow body of the syringe SR.

The longitudinally slidable hollow rod 29 comprises a distal portion or pusher 69 provided with an annular portion 69a extending radially towards the outside of the rod 29, and a longitudinal portion 69b extending axially from said annular portion 69a. Said pusher 69 is apt to be received in a seat SD provided in the sliding plunger SF which causes exit of the drug from the syringe SR.

Said seat SD provided in the plunger SF receives the pusher 69 preferably with some interference, in order to prevent occurrence of the so-called free-flow phenomenon, i.e. the exit of the drug from the syringe also in the absence of infusion by the apparatus, because of the pressure in hydrostatic pressure due to the position in which the apparatus may be arranged relative to the patient's body associated with the apparatus.

Figure 4:
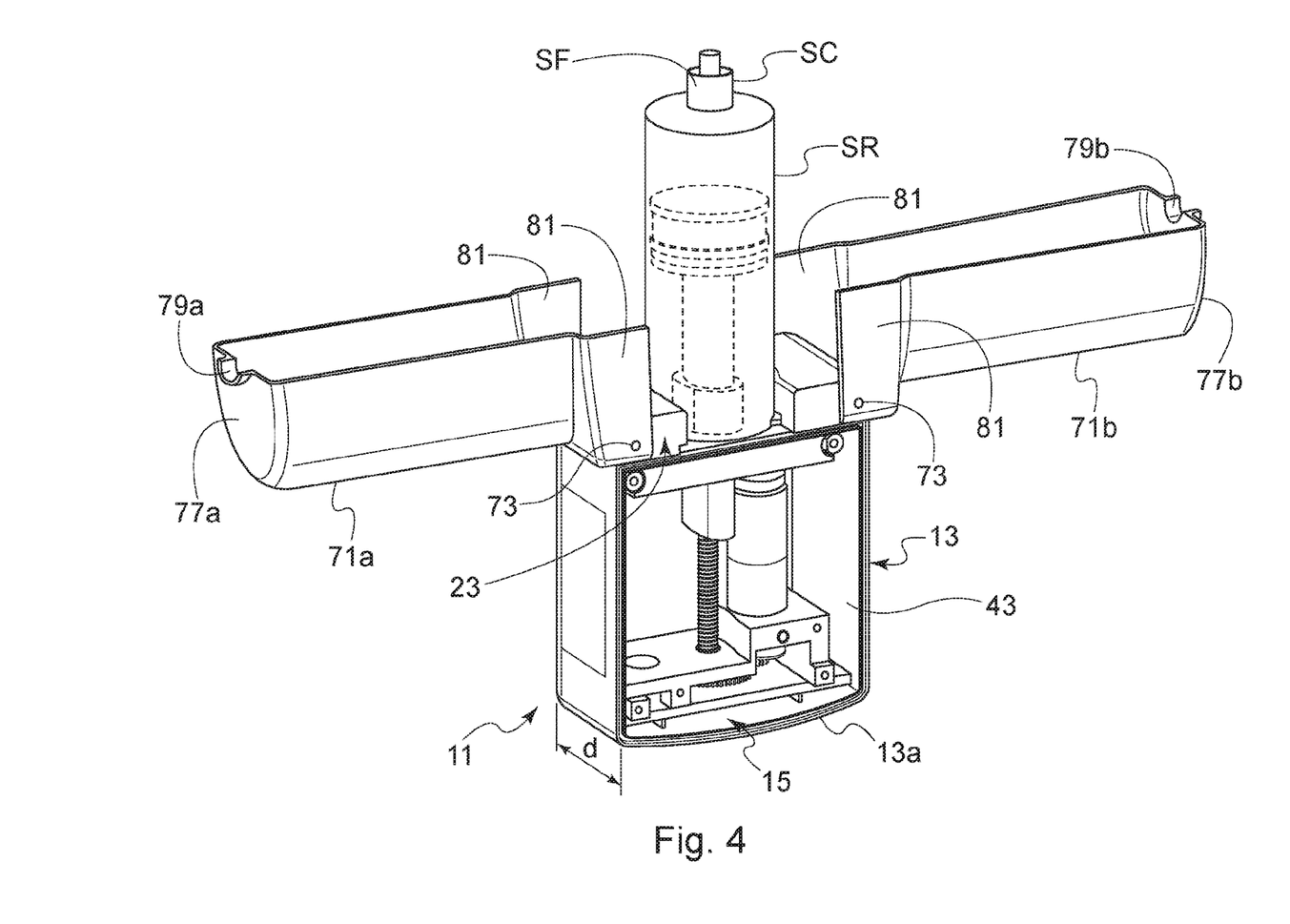
FIG. 4 is a perspective view of the apparatus of FIG. 1 provided with a protective bell in its open condition.
Figure 5:
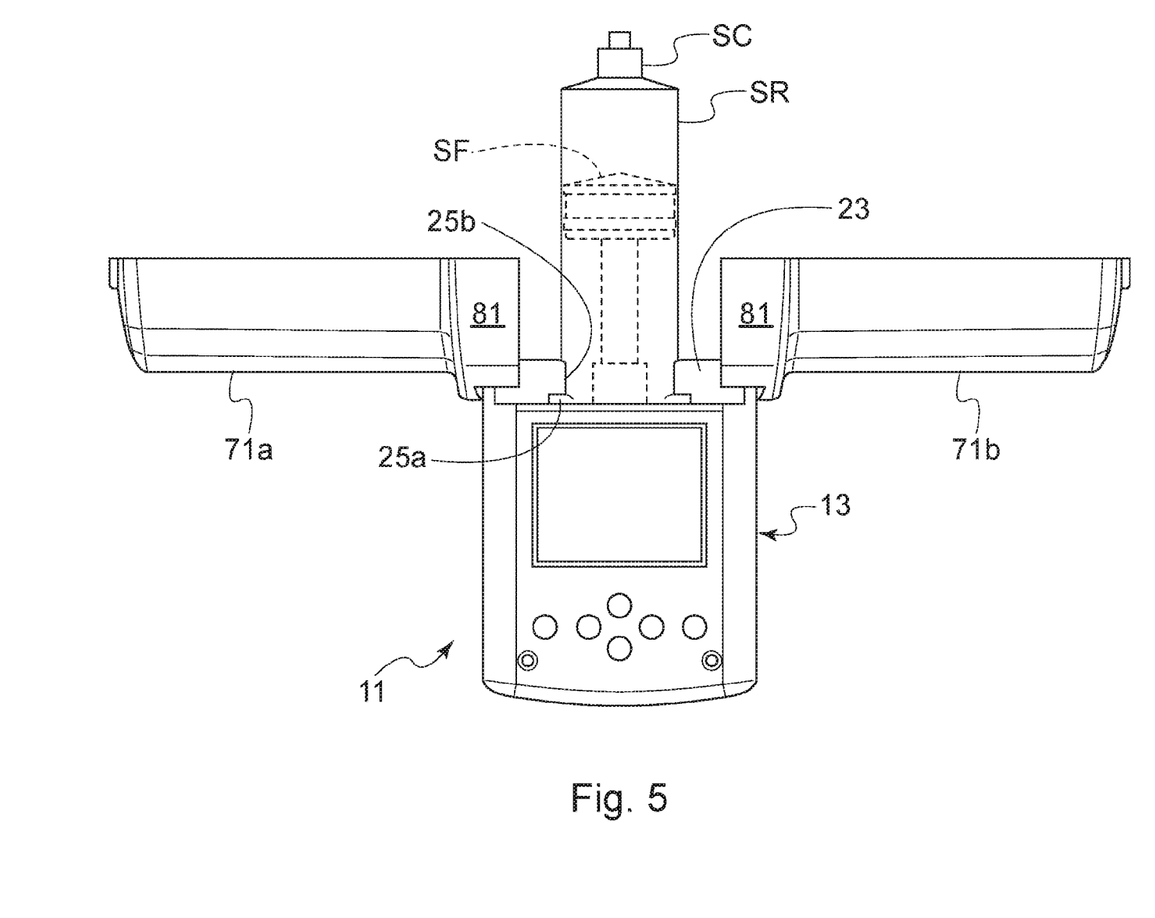
FIG. 5 is a plan view of the apparatus of FIG. 1 provided with a protective bell in its open condition.
Figure 6:
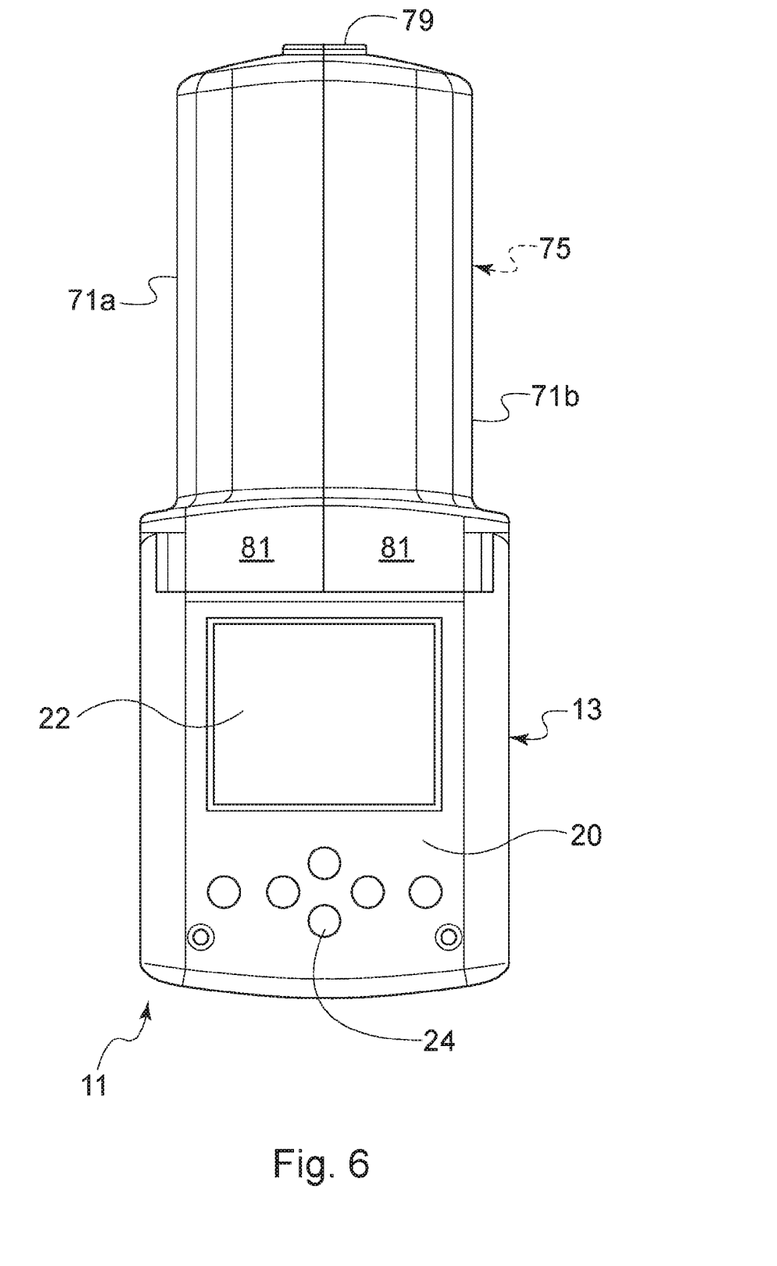
FIG. 6 è is a plan view of the apparatus of FIG. 1 provided with a protective bell in its closed condition.

Referring now to FIGS. 4 to 6, there is illustrated a shell 11 according to the invention provided with a protective bell 71 for the syringe SR associated with the infusion apparatus. The bell 71 mainly comprises a pair of half-shells 71a, 71b preferably hinged at the base at hinge pins 73. In the illustrated embodiment, the half-shells 71a, 71b are hinged to the ferrule 23, which ferrule is in turn preferably incorporated in the body of the casing 13. According to the invention, the half-shells 71a, 71b can assume, by rotating continuously around the hinge pins 73, an open configuration (FIGS. 4 and 5), in which the syringe SR is accessible to be inserted into and removed from the shell 11, and a closed configuration (FIG. 6), in which the syringe SR is substantially completely hidden from view. The half-shells 71a, 71b have a substantially "C"-shaped cross-section and consequently define inside them, when closed, a corresponding substantially cylindrical chamber 75 to house the syringe SR. Advantageously, the half-shells 71a, 71b have on the top, i.e. in the portion opposite to the hinge pins 73, a transverse base 77a, 77b with a corresponding recess 79a, 79b defining a corresponding passage 79, when the half-shells are closed, for the front end SC of the syringe SR from which the drug comes out during infusion. Advantageously, in addition, the half-shells 71a, 71b, when closed, define a substantially oval cross-section and are made in such a way as to be aesthetically incorporated in the body of the shell 11, following the external profile thereof. Said half-shells are also preferably made of plastics, of the same material as the casing. In particular, according to the illustrated embodiment, said half-shells 71a, 71b comprise at the base a pair of parallel wings 81 extending parallel to the ferrule 23 in parallel to the opposite major bases 19, 21 of the shell 11. Said wings 81 are advantageously made so as to interfere with the outer lateral surface of said ferrule 23, without, however, jeopardizing the smoothness of the opening and closing movement of the half-shells 71a, 71b, and so as to advantageously allow to keep the half-shells 71a, 71b closed, thus hiding the syringe SR associated with the shell 11. In order to improve locking of the rotation of the half-shells 71a, 71b it is also possible to provide one or more locking teeth between said wings 81 and the ferrule 23.

In addition, said half-shells 71a, 71b are preferably made of plastics, of the same material as the casing 13.

The invention as described and illustrated is susceptible to several variations and modifications, all of which fall within the same inventive principle.

The invention claimed is:

1. A portable electromechanical apparatus for drug infusion through a syringe (SR) provided with a corresponding slidable plunger (SF), said apparatus comprising:
   an electromechanical driving unit including an electric geared motor (43) and a rod (29) for exerting an axial thrust onto a slidable plunger of a syringe when engaged to the apparatus;
   a shell (11) comprising an outer monolithic casing (13) and a support structure (15), said casing (13) being made entirely of plastic and having a continuous and endless ring shape, said support structure being housed within the casing (13);
   wherein said support structure (15) is made entirely of metal; and
   wherein said casing (13) comprises a coupling ferrule (23) incorporated in a body of the casing (13) for firmly connecting a syringe (SR) to the shell of the portable electromechanical apparatus, said coupling ferrule (23) defining a bayonet-like coupling for a syringe (SR);
   wherein said shell includes a guide member (27) and said rod (29) is longitudinally slidable within said guide member (27);
   wherein said rod (29) has an axial cavity (49) with an open base (51) receiving a rotatable screw (53) engaged with a corresponding thread of an internally threaded nut or bushing (55) housed within said axial cavity (49) at said open base (51) of said rod (29);
   wherein said electric geared motor (43) has a driving shaft (57) with a pinion (59) having teeth engaged with a toothed gear wheel (61) fixed to a base of said rotatable screw (53);
   wherein said electric geared motor (43) being able to rotate said pinion (59) in opposite directions of rotation such that engagement of the pinion (59) and the toothed gear wheel (61) causes rotation of the screw (53) and, in turn, sliding of the rod (29) back and forth through the guide member (27);
   wherein said support structure (15) comprises a base plate (31) and a frame (33) fixed to the plate (31);
   wherein a seat (37) housing said driving shaft (57), said pinion (59), and said toothed gear wheel (61) is defined between the base plate (31) and the frame (33); and
   wherein the base plate (31) is flat and rests against a plurality of rest elements (41) incorporated in the body of the casing (13) and extending longitudinally and transversely within a chamber (17) defined within the casing (13) of the shell (11);
   whereby stress exerted by the screw (53) during a drug infusion is discharged against said rest elements (41).

2. The portable electromechanical apparatus according to claim 1, wherein said casing (13) defines a shape substantially rectangular in plan and defines therein the chamber (17) having a corresponding shape in which said support structure (15) is housed, and wherein flanks of the casing (13) have substantially the same width ("d") over an entire perimeter so as to obtain high stiffness and strength of the ring shape of said monolithic casing (13).

3. The portable electromechanical apparatus according to claim 2, wherein said casing (13) surrounds at least four flanks of said chamber (17) and opposite bases (19, 21), and wherein at least one of the opposite bases (19, 21) of said casing (13) is open.

4. The portable electromechanical apparatus according to claim 3, wherein said guide member (27) is incorporated in the body of said casing (13).

5. The portable electromechanical apparatus according to claim 2, wherein said guide member (27) is incorporated in the body of said casing (13).

6. The portable electromechanical apparatus according to claim 1, wherein said guide member (27) is incorporated in the body of said casing (13).

7. The portable electromechanical apparatus according to claim 6, wherein said sliding rod (29) and said guide member (27) have a non-circular cross-section, whereby rotation of said sliding rod (29) relative to the guide member (27) is prevented.

8. The portable electromechanical apparatus according to claim 6, wherein said support structure (15) is firmly but detachably associated within the casing (13) in a distal position relative to said guide member (27).

9. The portable electromechanical apparatus according to claim 1, wherein said support structure (15) is firmly but detachably associated within the casing (13) in a distal position relative to the guide member (27).

10. The portable electromechanical apparatus according to claim 1, wherein said sliding rod (29) and said guide member (27) have a non-circular cross-section, whereby rotation of the sliding rod (29) relative to the guide member (27) is prevented.

* * * * *